United States Patent [19]

Gabelman et al.

[11] Patent Number: 5,783,429
[45] Date of Patent: *Jul. 21, 1998

[54] ENZYMATIC OXIDATION OF ALCOHOLS TO ALDEHYDES IN A CONTINUOUS REACTION SYSTEM

[75] Inventors: Alan Gabelman. West Chester, Ohio; Gary A. Luzio, Newark, Del.

[73] Assignee: Givaudan Roure Flavors Corporation, Cincinnati, Ohio

[*] Notice: The term of this patent shall not extend beyond the expiration date of Pat. No. 5,593,872.

[21] Appl. No.: 728,085

[22] Filed: Oct. 9, 1996

Related U.S. Application Data

[63] Continuation-in-part of Ser. No. 524,911, Sep. 8, 1995, Pat. No. 5,593,872, which is a continuation of Ser. No. 165,748, Dec. 10, 1993, abandoned.

[51] Int. Cl.$^6$ .................................................. C12P 7/24
[52] U.S. Cl. ........................... 435/147; 435/911; 435/921
[58] Field of Search ................................ 435/147, 921, 435/911

[56] References Cited

U.S. PATENT DOCUMENTS

| | | | |
|---|---|---|---|
| 4,481,292 | 11/1984 | Raymond | 435/147 |
| 4,720,457 | 1/1988 | Armstrong et al. | 435/135 |
| 4,845,033 | 7/1989 | Tegtmeier | 435/162 |
| 4,871,669 | 10/1989 | Murray et al. | 435/147 |
| 4,900,670 | 2/1990 | Zall et al. | 435/147 |
| 4,904,590 | 2/1990 | Fukuda et al. | 435/147 |
| 4,920,055 | 4/1990 | Hoiberg et al. | 435/147 |
| 4,962,031 | 10/1990 | Yoshida et al. | 435/280 |
| 5,010,005 | 4/1991 | Duff et al. | 435/147 |
| 5,182,199 | 1/1993 | Hartley | 435/162 |
| 5,234,827 | 8/1993 | Hatfield et al. | 435/147 |

OTHER PUBLICATIONS

Duff S.J.B. et al., "Production and Application of Methylotrophic Yeast *Pichia Pastoris*", Biotech & Bioeng. 31: 44–49 (1988).

Kemp et al., "Inducible long chain alcohol oxidase from alkane-grown *Candida tropicalis*", Appl. Microbiol. Biotechnol. (1988) 29:370–374.

Murray et al., "Induction and stability of alcohol oxidase in the methylotrophic yeast *pichia–pastoris*.", Appl. Microbiol. Biotechnol. (1989) 32;95–100.

Duff et al., "Factors affecting the yeast–mediated conversion of ethanol to acetaldehyde in batch reactors", Enzyme Microb. Technol. (1989) 11:770–775.

Primary Examiner—Sandra E. Saucier
Attorney, Agent, or Firm—Wood, Herron & Evans, L.L.P.

[57] ABSTRACT

A process for the enzymatic oxidation of alcohols to aldehydes in a continuous reaction series is disclosed utilizing crude cellular methanol oxidase and catalase produced by an acceptable organism such as those selected from the genera of Pichia, Hansenula, Candida and Torulopsis. The process maintains a steady-state aldehyde concentration whereby enzyme activity is promoted. In particular, the process has two reactors operating in series continuously producing a fermenter effluent containing growing, intact yeast cells at a cell concentration of about 0.5 to about 3% by weight of the effluent by continuous culture of the cells on a methanol carbon source, continuously introducing the effluent from the first reactor to the second reactor, adding an alcohol feed at about 0.2–10% w/w and oxygen to the second reactor, maintaining a steady-state aldehyde concentration in the reaction mixture, the concentration of residual alcohol being about 0.1–9% w/w by controlling the rates of introduction of effluent and alcohol feed.

9 Claims, 1 Drawing Sheet

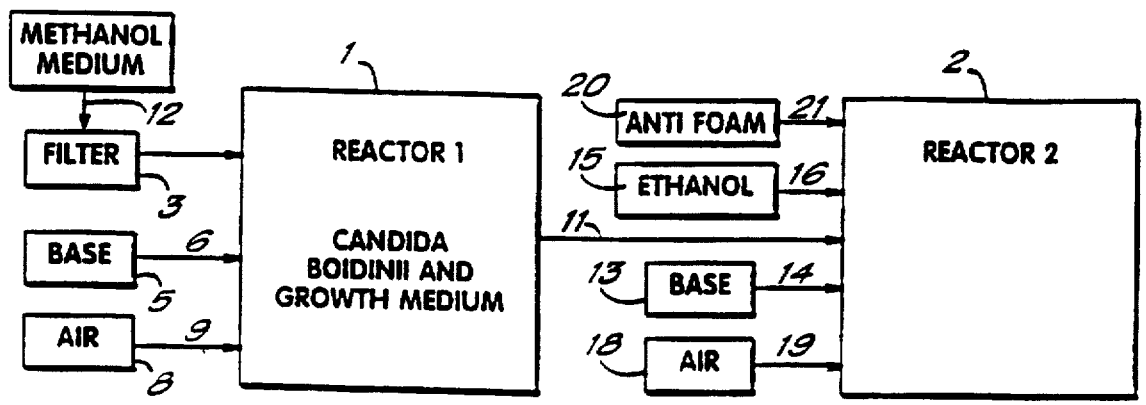

ENZYMATIC OXIDATION OF ALCOHOLS TO ALDEHYDES IN A CONTINUOUS REACTION SYSTEM

RELATED PATENT APPLICATION

The present invention is a continuation-in-part of U.S. patent application Ser. No 08/524,911 filed Sep. 8, 1995 now U.S. Pat. No. 5,593,872 entitled "Enzymatic Oxidation of Alcohols to Aldehydes in a Continuous Reaction System Using Candida boidinii", which is a continuation of U.S. patent application Ser. No. 08/165,748 filed Dec. 10, 1993 entitled "Enzymatic Oxidation of Alcohols to Aldehydes in a Continuous Reaction System", now abandoned.

FIELD OF THE INVENTION

This invention relates generally to the production of aldehydes from alcohols. More particularly, this invention relates to a process for the production of aldehydes in a continuous reaction by the enzymatic oxidation of alcohols utilizing crude alcohol oxidase and catalase produced by the yeast *Candida boidinii* or other acceptable organisms such as those selected from the genera of Pichia, Hansenula, Torulopsis and other organisms selected from the genus Candida.

BACKGROUND OF THE INVENTION

Aldehydes are important chemicals in the food industry. They serve as natural flavor additives to many food products. A preference among consumers for natural flavors exists as people are becoming more conscientious about their health and diet. Acetaldehyde is especially utilized by the food manufacturers as it provides a fresh flavor to many and various food products such as meats and breads. Acetaldehyde is important also for the synthesis of other desired products such as acetic acid and butanol.

Several methanol-utilizing microorganisms are capable of producing alcohol oxidase. These include yeasts of the genera Pichia, Hansenula, Candida, and Torulopsis, just to name a few. This alcohol oxidase can then be used in the process of oxidizing alcohols such as ethanol into aldehydes such as acetaldehyde.

U.S. Pat. No. 4,481,292 was issued for the production of acetaldehyde from ethanol using an enzyme complex containing alcohol dehydrogenase, NADH, flavin mononucleotide, and a catalase. The '292 process requires intricate steps of purification, separation and removal of components of the enzyme complex and products. This requires increased operational complexity and increased time, thus reducing the economic feasibility.

U.S. Pat. No. 4,920,055 was issued for the production of an aldehyde and hydrogen peroxide from alcohols having five or fewer carbon atoms, utilizing a methanol oxidase produced by *Hansenula polymorpha*. The '055 process uses a cell extract which is costly and results in yield loss. All examples in the '055 patent utilize purified enzymes. The process of purification reduces the economic feasibility of the process, as it takes time and money to purify the extract. Another disadvantage of the '055 process is that the enzyme is maintained in the system by either immobilization or recycling by use of membranes. Maintenance of the sufficient enzyme activity tends to be difficult by such immobilization and/or recycling.

SUMMARY OF THE INVENTION

This invention provides an economically feasible process for the continuous oxidation of alcohols to aldehydes. Crude enzymes produced by methanol-using organisms are used to oxidize the alcohols. Enzymes are continuously produced to oxidize the alcohols, thus maintaining sufficient enzyme activity.

The method of this invention involves enzymatically oxidizing alcohols to aldehydes in a continuous reaction system. The reaction system has two reactors operated in series. In a first reactor an organism, such as *Candida boidinii*, produces methanol oxidase and catalase enzymes. These enzymes are then removed without purification from the first reactor and combined with an aliphatic alcohol or aryl substituted aliphatic alcohol and oxygen in a second reactor, forming a reaction mixture. The alcohol in the second reactor is oxidized to its aldehyde. A steady-state aldehyde concentration in the reaction mixture of the second reactor is maintained. The enzyme activity in the second reactor is promoted, while other side reactions are eliminated. The aldehyde from the reaction mixture in the second reactor is then recovered.

In other subsidiary aspects of the invention, methanol oxidase oxidizes primary alcohols having 2 to 7 carbons. These alcohols include aryl substituted aliphatic alcohols such as benzyl alcohol, as well as aliphatic alcohols such as ethanol, n-propanol, n-butanol, 2-chloroethanol, 2-bromoethanol, allyl alcohol, 2-buten-1-ol and mixtures thereof. In another aspect of the invention, the catalase reduces hydrogen peroxide in the second reactor to release half of the oxygen required for the oxidation of the primary alcohol. Air is preferably added to reactor 2 and additional hydrogen peroxide may also be added. This additional hydrogen peroxide will be reduced by catalase already present, and will provide the additional oxygen required for the reaction. This invention overcomes disadvantages associated with prior processes of the type maintained in the background above.

Various organisms may be used to produce methanol oxidase and catalase enzymes such as *Pichia pastoris, Pichia pinus, Pichia trehalophila, Pichia molischiana, Hansenula polymorpha*, yeasts of Torulopsis and Candida, and all those yeasts which are genetically and/or taxonomically closely related to Pichia, Hansenula, Torulopsis and Candida genera.

Additional objects, advantages and novel features of the invention will be set forth in part in the description which follows, and others will become apparent to those skilled in the art upon examination of this description or may be learned by practice of the invention. The objects and advantages of the invention may be realized and attained by means of the instrumentalities and combinations particularly pointed out in the appended claims. The preferred embodiment is shown and described simply by way of illustration of the best mode contemplated of carrying out this invention. Accordingly, the FIGURE and description are to be regarded as illustrative in nature and not as restrictive.

BRIEF DESCRIPTION OF THE FIGURE

The FIGURE is a diagram of a continuous two-reactor system for oxidizing an alcohol to an aldehyde according to this invention.

DETAILED DESCRIPTION OF PREFERRED EMBODIMENT

The preferred process of oxidizing alcohols to aldehydes uses methanol oxidase produced by certain microorganisms such as yeasts of the genera Pichia, Candida, Hansenula and Torulopsis, and those which are closely related to these genera. Other suitable yeasts may, however, be used also. The process of the present invention involves the growth of a methanol-utilizing organism such as *Candida boidinii* on methanol at a cell density or concentration of about 0.5 to about 3% in the first reactor to produce methanol oxidase and catalase. Methanol is used as a carbon source for the microorganism. The microorganism is grown in continuous culture on the methanol medium. This medium is introduced to the fermenter in the first reactor where oxidase and catalase are generated by the organism.

The fermenter effluent containing intra-cellular methanol oxidase and catalase is introduced into the second reactor without purification. A major advantage of this invention is that extraction of the enzymes from the cells is not necessary. Also introduced into the second reactor is an aliphatic alcohol, or aryl substituted aliphatic alcohol containing 2 to 7 carbons so that a reaction mixture is formed, particularly in a concentration of about 0.2 to about 10% by weight feed alcohol. Air is preferably continuously pumped into the second reactor and the methanol oxidase oxidizes the alcohol into the aldehyde and hydrogen peroxide. The hydrogen peroxide is then reduced to water and oxygen. As crude cellular enzymes in the fermenter effluent from the first reactor are continually being added to the second reactor, the enzymes in the second reactor are replenished and the necessary enzyme activity is maintained. Therefore, the enzymes oxidize the alcohol in the second reactor producing its aldehyde. The catalase in the second reactor reduces hydrogen peroxide to produce hydrogen and water. This removes the hydrogen peroxide from the reaction mixture, eliminating any unwanted side reactions, and providing part of the oxygen for the oxidation reaction. The residual alcohol concentration in the second reactor is maintained particularly about 0.1 to about 9% by weight of the reaction mixture. The process of the invention, using crude alcohol oxidase and catalase produced by a microorganism, thus oxidizes alcohols to aldehydes in an economically feasible manner.

EXAMPLE 1

The combinations and interactions of the features described above can be more easily illustrated with reference to the schematic diagram of a continuous reaction system shown in the FIGURE.

In the first reactor 1, having a working volume of 10 liters, a concentration of about 2% of *Candida boidinii* is grown on a methanol medium in continuous culture. The medium contains the following per liter of deionized water; 3.14 ml (86% strength) phosphoric acid; 2.12 g potassium hydroxide pellets; 2.11 g $MgSO_4.7H_2O$; 0.098 g $CaCl_2.2H_2O$; 0.068 g NaCl; 0.47 ml (96% strength) $H_2SO_4$; 1.10 ml ammonium hydroxide (29% as $NH_3$); 1.5 mg biotin; 58 g methanol; and 16.3 ml micronutrient solution. The micronutrient solution is composed of the following per liter of deionized water: 1.89 g $FeSO4.7H_2O$; 0.99 g $ZnSo_4.7H_2O$; 0.471 g $NaMo_4$; 0.09 g KI; 0.075 g $MnSO_4.H_2O$; 0.06 g $CoCl_2.6H_2O$; 0.06 g $CuSO_4.5H_2O$; and 5.5 g citric acid.

A 0.2u sterilizing filter 3 sterilizes the methanol medium as it passes through an outlet 12 and through the filter 3 at a volumetric dilution rate of 0.08/hr. The growth medium ferments in the stirred reactor 1, with a pH maintained at about 2.5 to about 8, normally about 3.5, by automatic addition of concentrated ammonium hydroxide 5 through an inlet 6. The stirring speed of this medium is 850 rpm. The temperature is maintained at about 20° C. to about 35° C., normally about 30° C., while the pressure is maintained at about 0 to about 3 atmospheres, normally about 6 psig. Air 8 is sparged into the first reactor 1 by way of an inlet 9 at a rate of 20 slpm. Foam is controlled by a mechanical foam breaker (not shown). Fermented effluent contains 0.1 unit/ml to about 20 units/ml, normally about 10 to about 13 units/ml oxidase, about 0.02% of residual methanol, and about 20 g/l of cell dry weight.

The fermented effluent from the first reactor 1 is pumped without purification through an outlet 11 into a stirred reactor 2. The second reactor 2 has a 10 liter working volume. The pH of the second reactor 2 is maintained at about 6 to about 8, normally about 7.2, by the addition of 50% w/w aqueous potassium hydroxide 13 through an inlet 14. About 92% ethanol 15 is added at about 3.6% by weight of the incoming fermented effluent through an inlet 16. The stirrer speed for this reaction mixture is 1,000 rpm. The temperature is maintained at about 5° C. to about 37° C., normally about 20° C. It should be understood that the lower the temperature, the higher the concentration of aldehyde produced. However, the oxidizing process is slow with lower temperatures. The higher the temperature, the lower the concentration of aldehyde produced. However, the oxidizing process is faster with higher temperatures. The pressure in the second reactor 2 is maintained at about 0 atmospheres to about 3 atmospheres, normally atmospheric. Air 18 is sparged into the second reactor 2 by way of an inlet 19, at a rate of about 0.1 to about 2 volumes air/volume liquid/min, normally about 0.3 vvm. Foam is controlled by addition of an anti-foam 20 through an inlet 21.

The reaction mixture maintains a steady state containing: about 1.3% w/w liquid acetaldehyde; about 2.67% w/w gaseous acetaldehyde; about 1.8% w/w residual ethanol; about 0.25% w/w gaseous ethanol. The acetaldehyde productivity is about 1.72 g/l-h.

EXAMPLE 2

The same reaction process steps, reactants and reaction conditions are employed as in Example 1 except that the yeast *Pichia pastoris* is grown on a methanol medium in continuous culture.

As like Example 1, the reaction mixture maintains a steady state containing: about 1.3% w/w liquid acetaldehyde; about 2.67% w/w gaseous acetaldehyde; about 1.8% w/w residual ethanol; about 0.25% w/w gaseous ethanol. The acetaldehyde productivity is about 1.72 g/l-h.

EXAMPLE 3

The same reaction process steps, reactants and reaction conditions are employed as in Example 1 except that the yeast *Hansenula polymorpha* is grown on a methanol medium in continuous culture.

As like Example 1, the reaction mixture maintains a steady state containing: about 1.3% w/w liquid acetaldehyde; about 2.67% w/w gaseous acetaldehyde; about 1.8% w/w residual ethanol; about 0.025% w/w gaseous ethanol. The acetaldehyde productivity is about 1.72 g/l-h.

EXAMPLE 4

The same reaction process steps, reactants and reaction conditions are employed as in Example 1 except that the yeast is selected from the genus Torulopsis and is grown on a methanol medium in continuous culture.

As like Example 1, the reaction mixture maintains a steady state containing: about 1.3% w/w liquid acetaldehyde; about 2.67% w/w gaseous acetaldehyde; about 1.8% w/w residual ethanol; about 0.25% w/w gaseous ethanol. The acetaldehyde productivity is about 1.72 g/l-h.

Having described the invention, other embodiments will be understood to a person of ordinary skill in the art.

What is claimed is:

1. A process for the enzymatic oxidation of alcohols to aldehydes in a continuous reaction system of two reactors operated in series comprising:

continuously producing a fermenter effluent containing growing intact methylotrophic yeast cells at a cell concentration of about 0.5 to about 3% by weight of the effluent by continuous culture of the yeast cells using a carbon source consisting essentially of methanol in a first reactor, said yeast cells having intracellular methanol oxidase and catalase activity;

continuously introducing the effluent from the first reactor without purification of the effluent, to a second reactor;

adding an alcohol feed and oxygen to the second reactor to form the reaction mixture, said reaction mixture comprising about 0.2% to about 10% by weight of said feed alcohol, the alcohol being selected from the group consisting of ethanol, n-propanol, n-butanol, 2-chloroethanol, 2-bromoethanol, allyl alcohol, 2-buten-1-ol, benzyl alcohol and mixtures thereof;

enzymatically oxidizing said alcohol in the reaction mixture to its aldehyde while maintaining a steady-state aldehyde and alcohol concentration in the reaction mixture wherein said alcohol concentration is about 0.1 to about 9% by weight of the reaction mixture by controlling the rates of introduction of said effluent and said alcohol feed to the reaction mixture; and recovering the aldehyde from the reaction mixture.

2. The process of claim 1 wherein said yeast cells are selected from the group consisting of the genera of Pichia, Hansenula, Torulopsis, and Candida.

3. The process of claim 1 wherein said yeast cells are selected from the group consisting of *Pichia pastoris, Pichia pinus, Pichia trehalophila, Pichia molischiana, Hansenula polymorpha,* and *Candida boidini.*

4. The process of claim 1 wherein said temperature of the first reactor is maintained at about 20° C. to about 35° C., pressure is maintained at about 0 atmospheres to about 3 atmospheres, and pH is maintained at about 2.5 to about 8.

5. The process of claim 1 wherein said temperature of the second reactor is maintained at about 5° C. to about 37° C., pressure is maintained at about 0 atmospheres to about 3 atmospheres, and pH is maintained at about 6 to about 8.

6. The process of claim 1 wherein oxygen is supplied by sparging air into the second reactor.

7. The process of claim 6 wherein said air is sparged at the rate of about 0.1 to about 2 volume air/volume liquid/min.

8. The process of claim 1 wherein oxygen is supplied by adding hydrogen peroxide to the second reactor which is reduced by said catalase.

9. The process of claim 1 wherein said oxidase concentration in the first reactor is about 0.1 units/ml to about 20 units/ml.

* * * * *